(12) United States Patent
Allen et al.

(10) Patent No.: US 9,360,440 B2
(45) Date of Patent: Jun. 7, 2016

(54) NON-HOMOGENEOUS SAMPLE HANDLING APPARATUS AND X-RAY ANALYZER APPLICATIONS THEREOF

(71) Applicant: X-RAY OPTICAL SYSTEMS, INC., East Greenbush, NY (US)

(72) Inventors: George Allen, Middle Grove, NY (US); John H. Burdett, Jr., Scotia, NY (US); Zewu Chen, Schenectady, NY (US); Leslie Johnson, Castleton, NY (US)

(73) Assignee: X-RAY OPTICAL SYSTEMS, INC., East Greenbush, NY (US)

( * ) Notice: Subject to any disclaimer, the term of this patent is extended or adjusted under 35 U.S.C. 154(b) by 31 days.

(21) Appl. No.: 14/208,215

(22) Filed: Mar. 13, 2014

(65) Prior Publication Data
US 2014/0270063 A1    Sep. 18, 2014

Related U.S. Application Data (60) Provisional application No. 61/790,517, filed on Mar. 15, 2013.

(51) Int. Cl.
*G01N 23/223*    (2006.01)
*B01L 3/00*    (2006.01)
(Continued)

(52) U.S. Cl.
CPC .......... *G01N 23/223* (2013.01); *G01N 23/2204* (2013.01); *G01N 35/085* (2013.01);
(Continued)

(58) Field of Classification Search
CPC .......... G01N 1/00; G01N 1/002; G01N 1/02; G01N 1/10; G01N 1/1056; G01N 1/14; G01N 1/18; G01N 1/28; G01N 21/03; G01N 21/0303; G01N 21/05; G01N 21/85; G01N 23/22; G01N 23/2202; G01N 23/2204; G01N 23/223; G01N 29/222; G01N 30/00; G01N 30/04; G01N 30/06; G01N 30/16; G01N 30/18; G01N 30/24; G01N 33/22; G01N 33/225; G01N 33/26; G01N 33/28; G01N 33/2835; G01N 35/00584; G01N 35/0429; G01N 35/0432; G01N 35/0434; G01N 35/08; G01N 35/085; G01N 2021/0193; G01N 2021/0307; G01N 2021/052; G01N 2021/058; G01N 2021/6482; G01N 2021/8557; B01L 3/56; B01L 3/561; H01J 37/00; H01J 37/18; H01J 37/20; H01J 37/20
USPC .............. 378/44, 47, 204, 208, 210; 250/253, 250/288, 216, 573, 576; 436/43, 52, 174, 436/180; 73/61.41, 61.43, 61.48, 61.59, 73/61.68, 64.56, 863, 863.01, 864.81, 73/864.82, 864.83, 864.84, 864.85, 73/864.86, 864.87, 864.91
See application file for complete search history.

(56) References Cited

U.S. PATENT DOCUMENTS 2,970,216 A * 1/1961 Magrath ........................ 250/428
4,888,998 A * 12/1989 Buzza et al. ............... 73/864.21

(Continued)

FOREIGN PATENT DOCUMENTS

KR    10-2005-0210698 A    12/2005

OTHER PUBLICATIONS

Allen et al., International Search Report (ISR) & Written Opinion for PCT Application No. PCT/US2014/025414, filed Mar. 13, 2014, dated Aug. 8, 2014 (16 pages).

*Primary Examiner* — Anastasia Midkiff
(74) *Attorney, Agent, or Firm* — Jeff Klembczyk, Esq.; Kevin P. Radigan, Esq.; Heslin Rothenberg Farley & Mesiti P.C.

(57) ABSTRACT

A sample handling apparatus/technique/method are provided for a material analyzer, including: a sample cell insert for carrying sample to and from a sample focal area of the analyzer; a removable sample carrying device for providing sample to the cell insert; and an actuator to flow sample from the carrying device to the sample cell insert. The removable sample carrying device may be a syringe, and the actuator pushes a plunger of the syringe to expel the sample to the sample cell insert. The sample cell insert may be mounted onto a sample cell, the sample cell being insertable into the analyzer for sample analysis. The sample handling apparatus may be used in combination with an optic-enabled x-ray analyzer, the x-ray analyzer including an x-ray engine with an x-ray excitation path and an x-ray detection path, wherein the x-ray excitation and/or the x-ray detection path define the sample focal area.

19 Claims, 11 Drawing Sheets

(51) Int. Cl.
*G01N 23/22* (2006.01)
*G01N 35/08* (2006.01)
*G01N 1/28* (2006.01)
*G01N 1/00* (2006.01)
*G01N 21/85* (2006.01)

(52) U.S. Cl.
CPC *B01L 3/561* (2013.01); *G01N 1/28* (2013.01); *G01N 21/85* (2013.01); *G01N 2001/002* (2013.01); *G01N 2223/076* (2013.01); *G01N 2223/637* (2013.01); *G01N 2223/652* (2013.01)

(56) References Cited

U.S. PATENT DOCUMENTS

| | | | |
|---|---|---|---|
| 5,776,418 A * | 7/1998 | Besnier et al. | 422/68.1 |
| 7,759,125 B2 | 7/2010 | Zhao | |
| 2008/0218761 A1 | 9/2008 | Nishikawa et al. | |
| 2009/0115434 A1* | 5/2009 | Hirthe et al. | 324/693 |
| 2009/0141867 A1 | 6/2009 | Burdett, Jr. et al. | |
| 2010/0135853 A1* | 6/2010 | Broga et al. | 422/51 |
| 2011/0034758 A1* | 2/2011 | Shany et al. | 600/35 |
| 2013/0044858 A1 | 2/2013 | Allen et al. | |
| 2014/0193918 A1* | 7/2014 | Takahashi et al. | 436/50 |

\* cited by examiner

FIG. 11b ically, the present invention is directed to flow control techniques for presenting # NON-HOMOGENEOUS SAMPLE HANDLING APPARATUS AND X-RAY ANALYZER APPLICATIONS THEREOF

RELATED APPLICATION INFORMATION

This application claims the benefit of U.S. provisional patent application Ser. No. 61/790,517, filed Mar. 15, 2013, which is hereby incorporated herein by reference in its entirety.

TECHNICAL FIELD

This invention relates in general to apparatus and methods used for analysis of samples. More particularly, the present invention is directed to flow control techniques for presenting a non-homogeneous sample to an analysis focal area in, e.g., an x-ray analysis system.

BACKGROUND OF THE INVENTION

X-ray analysis of samples is a growing area of interest across many industries such as consumer products, medical, pharmaceutical, and petroleum. The use of x-ray fluorescence, x-ray diffraction, x-ray spectroscopy, x-ray imaging, and other x-ray analysis techniques has led to a profound increase in knowledge in virtually all scientific fields.

X-ray fluorescence (XRF) is an analytical technique by which a substance is exposed to a beam of x-rays to determine, for example, the presence of certain components. In XRF, at least some of the elemental constituents of the substance exposed to x-rays can absorb x-ray photons and produce characteristic secondary fluorescence. These secondary x-rays are characteristic of the elemental constituents in the substance. Upon appropriate detection and analysis these secondary x-rays can be used to characterize one or more of the elemental constituents. XRF techniques have broad applications in many chemical and material science fields, including industrial, medical, semiconductor chip evaluation, petroleum, and forensics, among others.

As some examples of measurements required in the petroleum industry, trace levels of contaminants in petroleum feedstocks is a notorious problem in petroleum refining. Sulfur is a common component in crude oil streams—and its removal from final product is mandated due to its impact on the environment, as regulated by the US EPA under the Clean Air Act. Sulfur is harmful to the environment, and the cost of its removal is high. Therefore, monitoring sulfur levels early in the refining process is important. Chlorine and vanadium contaminants are considered "bad actors" by the refining industry for primarily non-regulatory, process control reasons. Chlorides also pose one of the greatest problems to the refining industry. According to a 2005 paper by The National Association of Corrosion Engineers ("NACE"): "Recently, an increasing number of refineries have experienced extreme corrosion and fouling in crude distillation unit overheads and/or naphtha hydrotreating units. The root causes were traced to severe spikes in the chloride levels."

U.S. Pat. Nos. 6,934,359 and 7,072,439, hereby incorporated by reference herein in their entirety and assigned to X-Ray Optical Systems, Inc., the assignee of the present invention, disclose monochromatic wavelength dispersive x-ray fluorescence (MWD XRF) techniques and systems for the analysis of liquid samples.

As one particular example of a measurement system for such contaminants, the above-incorporated patents disclose techniques for the determination of the level of elements in petroleum fuels, and commercialized analyzers (e.g., SINDIE™ and CLORA™) are now in widespread use for, e.g., sulfur and chlorine measurement at petroleum refining, pipeline, and/or terminal facilities.

XRF testing can take place off-line, i.e., using a bench-top, laboratory-type instrument to analyze a sample. The material is removed from its source (e.g., for fuel, from a refinery or transportation pipeline) and then deposited in a sample chamber; or into a windowed sample cell which is then deposited into a chamber. Off-line, bench-top instruments need not meet any unusual operational/pressure/environmental/size/weight/space/safety constraints, but merely need to provide the requisite measurement precision for a manually-placed sample. Moreover, off-line instruments can be easily maintained between measurements.

In contrast to off-line analysis, on-line analysis provides "real-time" monitoring of sample composition at various points in the manufacturing process. For example, all fuel products are subject to sulfur level compliance—requiring some variant of on-line monitoring during fuel refining and transportation in pipelines. On-line analysis of fuels in a refinery and in pipelines, however, requires consideration of numerous operational issues not generally present in an off-line, laboratory setting. A fully automated fuel sample handling system is required—with little or no manual intervention or maintenance. Also, since fluids are usually under pressure in pipelines, any sample handling system must account for pressure differentials. This is especially important since certain portions of XRF x-ray "engines" (discussed further below) operate in a vacuum. Also, the instrument's electronics require packaging in an explosion-proof housing—separate from the sample handling system.

In either analyzer, for crude and heavy fuel applications, differing sample stream viscosities make it challenging to present samples to the analyzer at a stable pressure and flow rate. Chlorine measurement presents another challenge because the chlorine mostly exists in water phase, which may not mix homogeneously in crude.

For typical homogeneous samples (e.g., finished petroleum product such as gasoline or diesel) in off-line analyzers (e.g., bench-top configurations) a safe assumption is that the analyte exists at a constant concentration throughout the volume of a sample cell, so an x-ray focal spot will produce the same measurement result throughout the volume. However, sample settling can occur for non-homogeneous samples in a sample cell. Portions of the sample (e.g., particulate) can either settle to the bottom or move to the top based on density and gravity and other factors. This potential sample movement/non-homogeneity within a sample cell (especially an XRF sample cell of the type discussed herein) presents measurement challenges, because the concentration of analyte at any particular focal point within the cell may not provide consistent measurement results.

What is required, therefore, are sample handling techniques for analysis systems handling high viscosity, non-homogeneous samples, which provide analyte measurement results representative of the overall concentration of the analyte in a sample volume, despite the presence of localized inconsistencies in the sample.

SUMMARY OF THE INVENTION

The shortcomings of the prior art are overcome and additional advantages are provided by the present invention which in one aspect is a sample handling apparatus/technique/method for a material analyzer, including a sample cell insert for carrying sample to and from a sample focal area of the analyzer; a removable sample carrying device for providing sample to the sample cell insert; and an actuator to flow sample from the carrying device to the sample cell insert.

The removable sample carrying device may be a syringe, and the actuator pushes a plunger of the syringe to expel the sample therefrom to the sample cell insert. The sample cell insert may be mounted onto a sample cell, the sample cell being insertable into the analyzer for sample analysis.

The sample handling apparatus may be used in combination with an x-ray analyzer, the x-ray analyzer including an x-ray engine with an x-ray excitation path and an x-ray detection path, wherein the x-ray excitation and/or the x-ray detection path defines the sample focal area.

The focal area may be a focal point, defined by focused x-rays to/from at least one focusing optic in the x-ray excitation path and/or the x-ray detection path. The focusing optic may be a curved diffracting optic or a polycapillary optic.

The system may comprise a monochromatic wavelength-enabled XRF analyzer; e.g., an MWDXRF or ME-EDXRF analyzer.

The sample may comprise a low or high viscosity petroleum-based product requiring the measurement of an analyte therein, e.g., one or more elements chosen from the following list: S, Cl, P, K, Ca, V, Mn, Fe, Co, Ni, Cu, Zn, Hg, As, Pb, and Se.

Further, additional features and advantages are realized by the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in combination with the accompanying drawings in which:

DETAILED DESCRIPTION OF THE INVENTION

Figure 1:
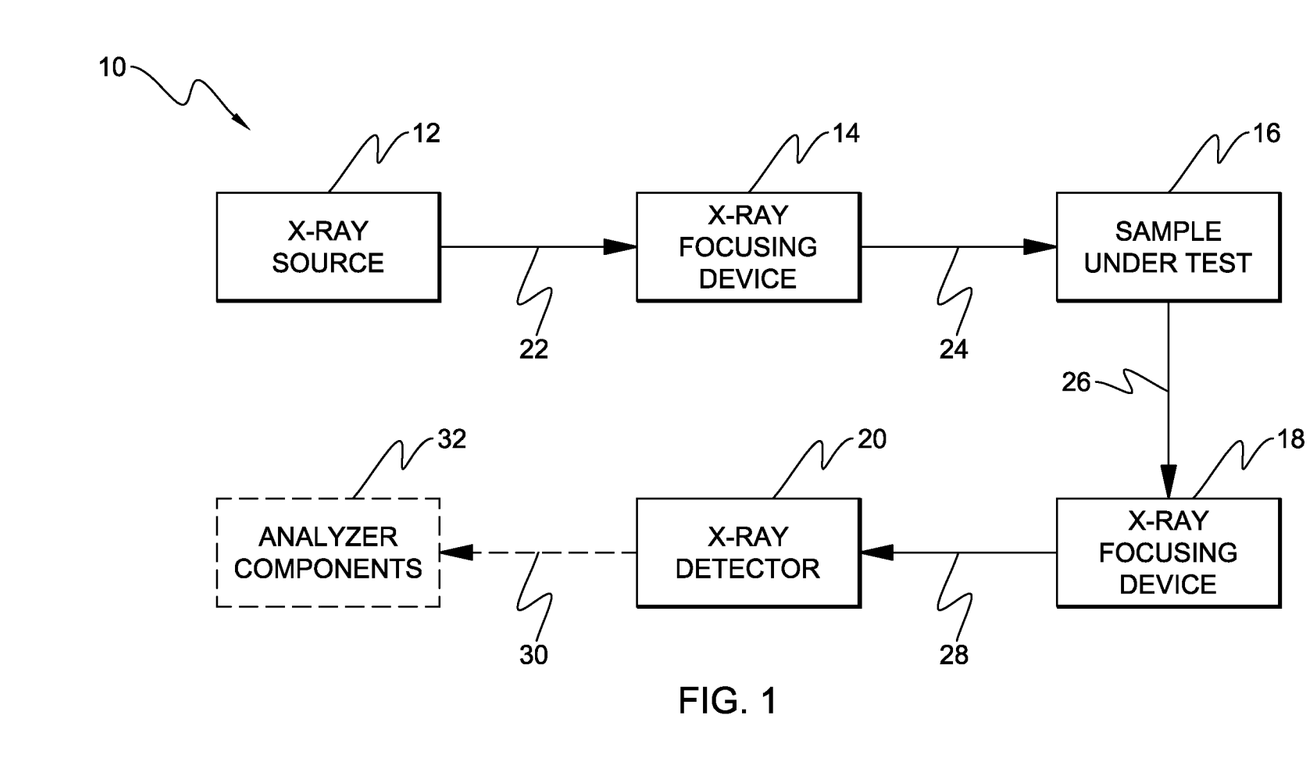
FIG. 1 is a functional block diagram of the elements of an exemplary x-ray fluorescence system.

FIG. 1 is a functional block diagram of an exemplary XRF system 10 used for exposing a sample to x-ray radiation to produce fluorescent radiation which can then be detected and analyzed to determine a characteristic of the sample. The system may include an x-ray source 12, a first x-ray focusing device 14, a sample under test 16, a second x-ray focusing device 18, an x-ray detector 20, and an analyzer components 32 for providing the analytical result. The x-ray source 12, for example, an x-ray tube, produces a beam of x-rays 22. Beam 22 may diffracted or focused by one or more x-ray focusing optics 14 as discussed further below.

When irradiated by beam 24, at least one of the constituents of sample in chamber 16 is excited in such a fashion that the constituent fluoresces, that is, produces a secondary source of x-rays 26 due to excitation by x-rays 24. Again, since x-ray beam 26 is typically a diverging beam of x-rays, beam 26 may be focused by the second x-ray focusing optics 18, for example, to produce a focused beam of x-rays 28 directed toward x-ray detector 20.

X-ray detector 20 may be a proportional counter-type or a semiconductor type x-ray detector (e.g., silicon drift detector), or any other suitable type of x-ray fluorescence detector known to one skilled in the art. Typically, x-ray detector 20 produces an electrical signal 30 containing a characteristic of the detected x-rays which is forwarded to an analyzer components 32 for analysis, printout, or other display.

X-ray focusing devices/optics 14, 18 for advanced XRF systems, including those below, may include, for example, curved crystal monochromating optics such as those disclosed in commonly assigned U.S. Pat. Nos. 6,285,506; 6,317,483; 7,035,374 and 7,738,629; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506; 7,209,545; and 7,257,193 are also useable. Each of the above-noted patents is hereby incorporated herein by reference in its entirety.

The following are two examples of x-ray-optic-enabled analyzer engines which may be used in connection with a sample handling apparatus, technique, or method of the present invention:

Exemplary MWD XRF X-Ray Analysis Engines:

The assignee of the present invention has previously disclosed a Monochromatic Wavelength Dispersive X-ray Fluorescence (MWD XRF) analyzer 120 using two monochromating optic sets (U.S. Pat. Nos. 6,934,359 and 7,072,439—hereby incorporated by reference herein in their entirety), as shown schematically in FIG. 2. The related SINDIE (Sulfur IN DIEsel) and CLORA (chlorine) product lines for the measurement of e.g., sulfur and chlorine in diesel fuel and other petroleum products revolutionized XRF and provide many advantages including: (1) signal/background (S/B) is improved due to monochromatic excitation of the sample by DCC1 14', i.e., the bremsstrahlung photons with energies under fluorescence peaks (which normally swamp these peaks of interest) can only reach the detector through scattering, therefore improving the S/B ratio dramatically compared to polychromatic excitation; (2) superior energy resolution—this eliminates all common interference problems and provides the physical basis for upstream applications; (3) inherent robustness and low maintenance—the analysis engine is low power, compact, with no moving parts or consumable gasses; and (4) unprecedented dynamic range, e.g., a quantification level from 0.3 ppm to 5% of sulfur in a sample.

Figure 2:
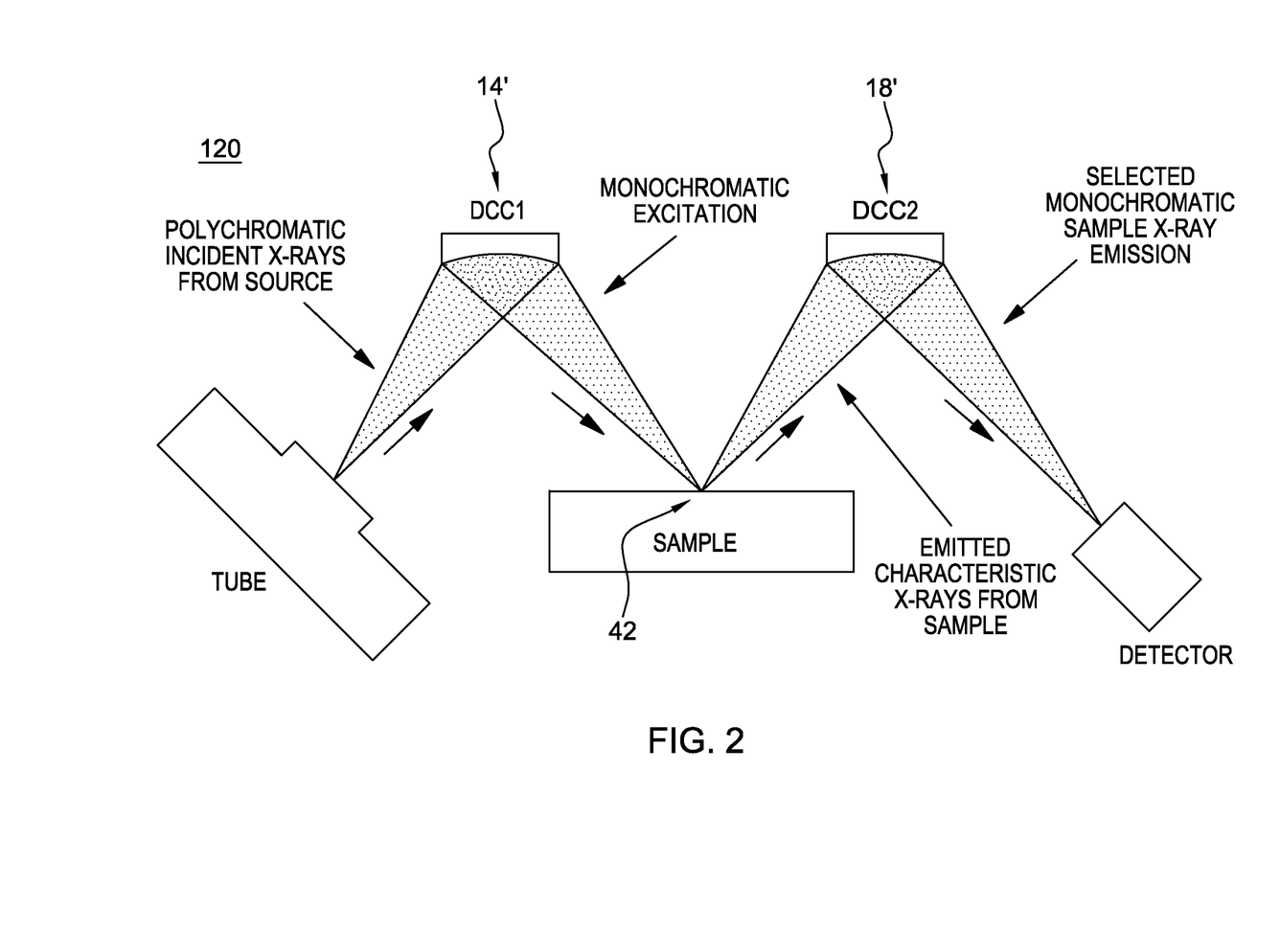
FIG. 2 is a schematic view of an exemplary MWD XRF x-ray engine useable with a sample handling apparatus, in accordance with one or more aspects of the present invention.

The MWD XRF engine 120, shown schematically in FIG. 2, includes curved monochromating optics 14' and 18' in the excitation and detection paths respectively, forming focal area or point 42 on the sample (discussed further below), which is the configuration of the SINDIE sulfur analyzer discussed above. However, an optic may only be present in one of these paths, which still requires precise alignment. In one example, an optic of any of the above-describe types may only be present in the excitation path, and the detection path would include an energy dispersive detector. This is the common configuration of an energy dispersive x-ray fluorescence (EDXRF) system, discussed further below.

Figure 3:
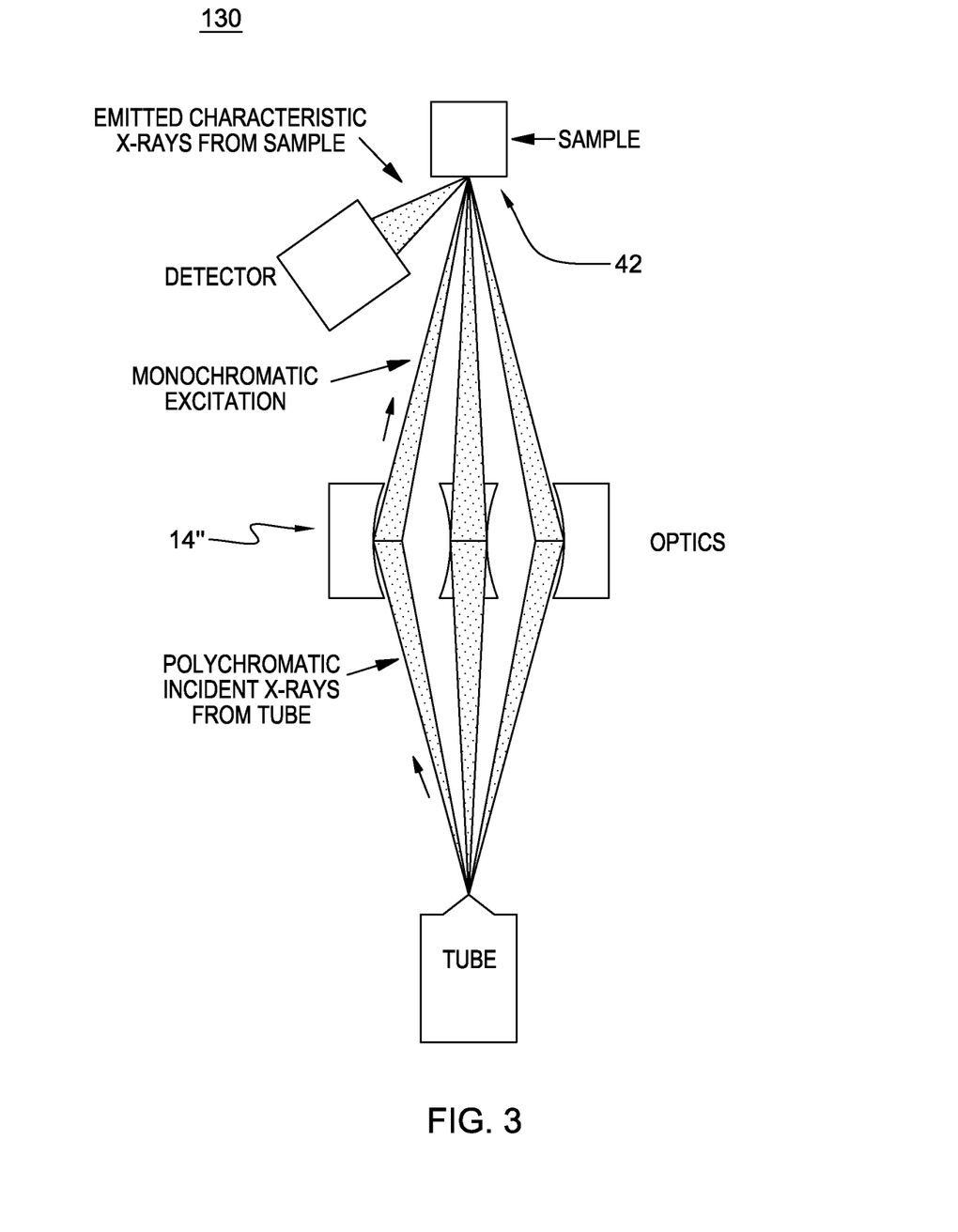
FIG. 3 is a schematic view of an exemplary ME EDXRF x-ray engine useable with a sample handling apparatus, in accordance with one or more aspects of the present invention.

Exemplary ME EDXRF X-Ray Analysis Engine:

Monochromatic excitation, energy dispersive x-ray fluorescence (ME-EDXRF) analyzers can also be used for this application, in accordance with the present invention. The engine technology is disclosed in, e.g., commonly assigned US Publication 2011-0170666A1 and PCT Publication No, WO 2009111454 (A1) entitled XRF System Having Multiple Excitation Energy Bands In Highly Aligned Package, the entireties of which are hereby incorporated by reference herein. In one embodiment this engine 130 involves monochromatic excitation known as HD XRF as depicted schematically in FIG. 3. HD XRF is a multi-element analysis technique offering significantly enhanced detection performance over traditional ED or WD XRF. This technique applies state-of-the-art monochromating and focusing optics 14" illuminating a focal area or point 42 on the sample, enabling multiple select-energy excitation beams that efficiently excite a broad range of target elements in the sample. Monochromatic excitation dramatically reduces scattering background under the fluorescence peaks, greatly enhancing elemental detection limits and precision.

Figure 4:
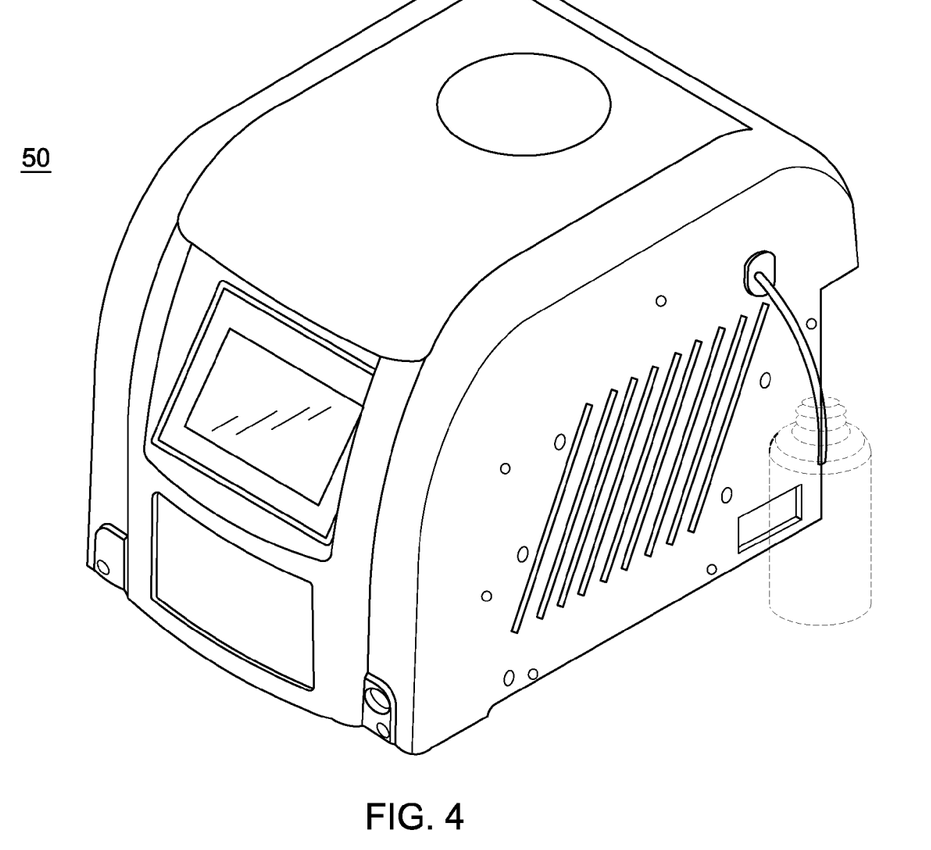
FIG. 4 is a perspective view of a typical bench-top x-ray analyzer useable with a sample handling apparatus, in accordance with one or more aspects of the present invention.

FIG. 4 is a perspective view of a typical bench-top x-ray analyzer 50 useable in connection with either of the engines above, or other analytical engines, and in combination with the sample handling apparatus of the present invention as discussed further below.

Figures 5A, 5B:
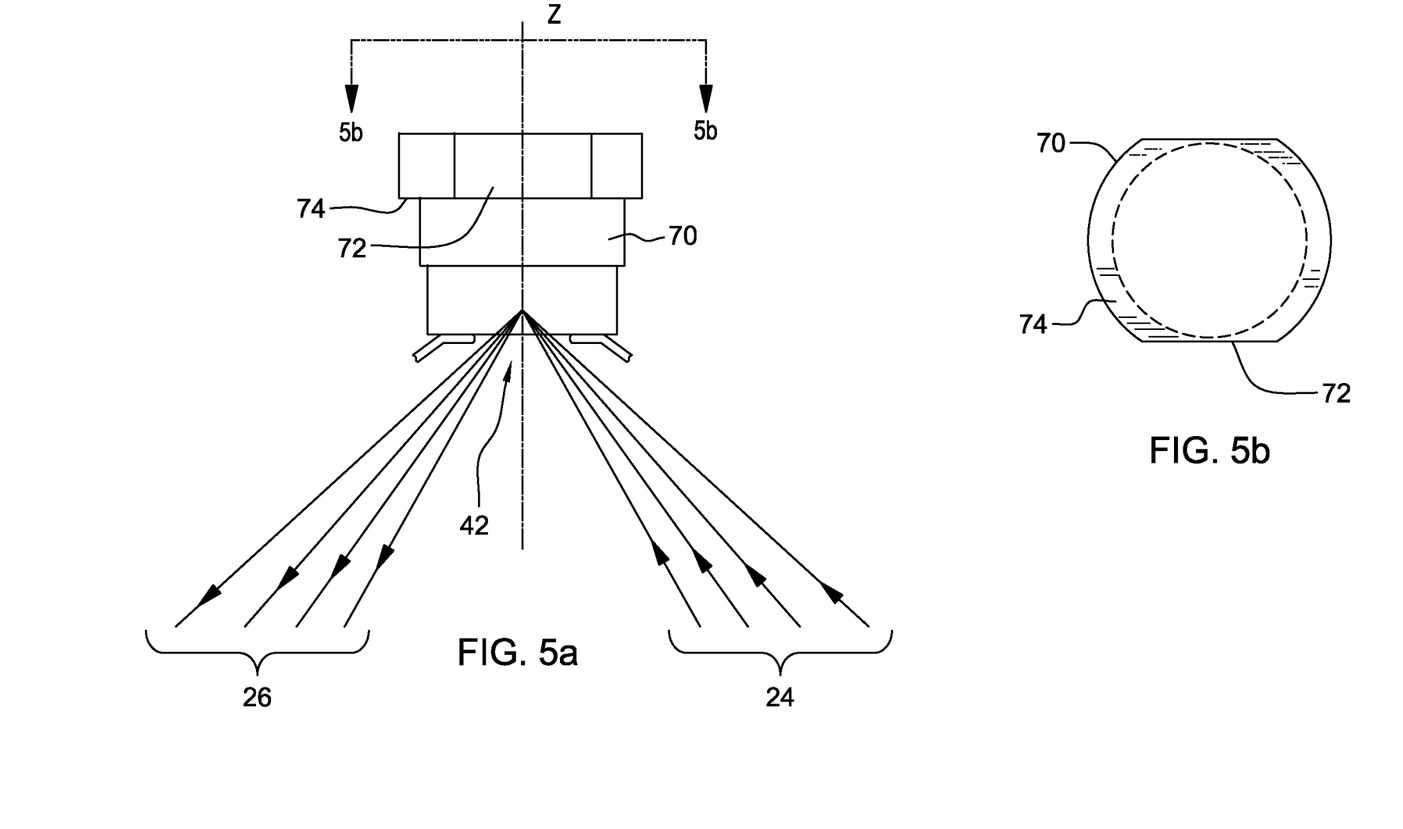
FIGS. 5a-b are side and top views of a sample cell useable with a sample handling apparatus, in accordance with one or more aspects of the present invention.

FIGS. 5*a-b* are side and top views of an exemplary sample cell useable in such an analyzer, and in combination with the sample handling apparatus of the present invention As disclosed in commonly assigned U.S. Pat. No. 7,729,471, the entirety of which is incorporated herein by reference, this sample cell may be a pre-filmed, precision sample cell 70. The sample cell includes an outer body forming an interior sample reservoir, the top end of which accepts a sample, and the bottom end of which may be pre-filmed for accepting input 24 and output 26 x-ray beams when placed in an analyzer, e.g., analyzer 50 of FIG. 6. As discussed above, sample focal area or point 42 is formed by these beams.

This lower end of the interior sample reservoir may be formed of a film (e.g., mylar) which can be wrapped tightly around the lower ends of the body, and held in place using a conformal ring. Other attachment techniques are possible, including glues, ultrasonic, RF, or other heating techniques to create a bond between the film and the body around the perimeter of the lower end. The film is preferably designed with enough strength to hold the sample (and, as discussed further below, with enough strength to support the entire sample cell in the instrument), while allowing penetration of x-rays, and resultant x-ray fluorescence from/to the x-ray analysis engine. The sample can be a liquid sample, a partially-liquid sample, or a solid (e.g., powder) sample.

Other features include opposing horizontal edges 74 which can assist/control the vertical placement of the cell in an x-ray analysis engine, and opposing faces 72 which can also be used to assist/control the horizontal/rotational placement of the cell. In accordance with the present invention, edges 74 and faces 72 can assist in attachment and removal of the sample cell insert of the present invention, as discussed further below.

Figure 6:
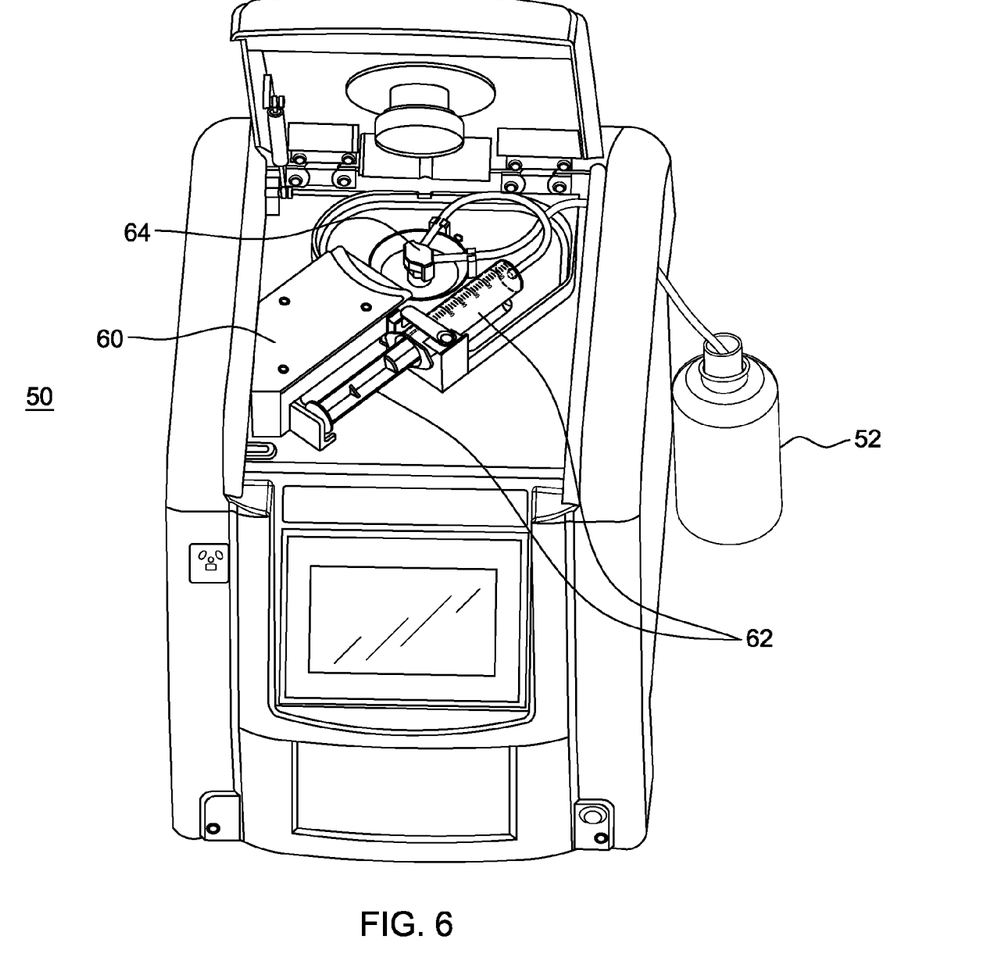
FIG. 6 is a perspective view of one embodiment of a sample handling apparatus in accordance with one aspect of the present invention implemented in an exemplary bench-top analyzer.

FIG. 6 is a perspective view of a sample handling apparatus 60 in accordance with one aspect of the present invention, implemented in an exemplary bench-top analyzer 50. Sample handling apparatus 60 is mounted inside the access door of analyzer 50 and over the sample chamber. In accordance with the present invention, removable syringe 62 (or more generally a removable sample carrying device) holds e.g., a non-homogeneous sample which is flowed through a sample cell insert 64 by activating the plunger of the syringe using an embedded motor. Sample is flowed from the syringe, through tubing, through the sample cell insert, through the analyzer focal area, and then expelled into an external bottle 52. The present invention advantageously supplements a standard bench-top analyzer 50 having a standard sample cell (e.g., sample cell 70) with a capability to flow a non-homogeneous sample though the sample cell. By flowing sample through the sample cell (and the focal area or point) during the time period of the XRF measurement (e.g., 1, 3, 6 minutes), any non-homogeneities are normalized and an average analyte concentration can be obtained. This is superior to an unpredictable, non-homogeneous sample statically held in the sample cell volume, which as discussed above may have locally different analyte concentrations such that the concentration at the focal area or point may not represent the concentration throughout the sample.

Figure 7:
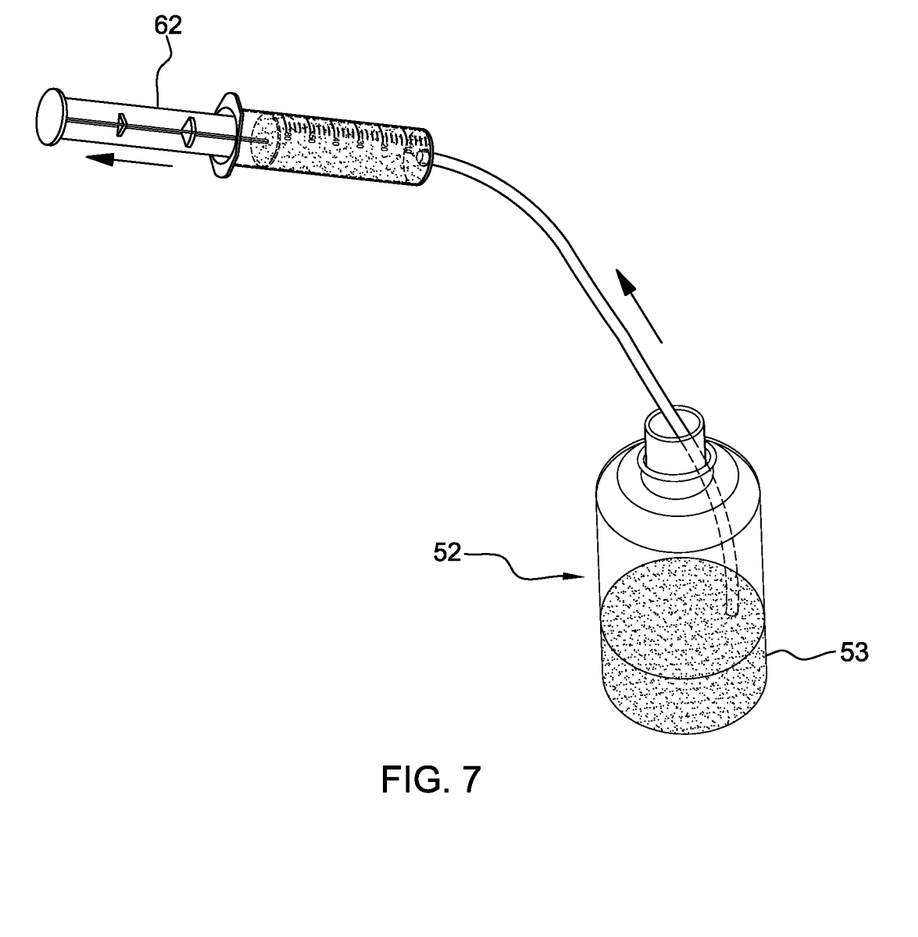
FIG. 7 shows a syringe extracting a non-homogeneous sample for analysis.

FIG. 7 shows removable syringe 62 extracting a non-homogeneous sample 53 (e.g., crude oil) from bottle 52 prior to analysis and insertion into the apparatus.

Figure 8:
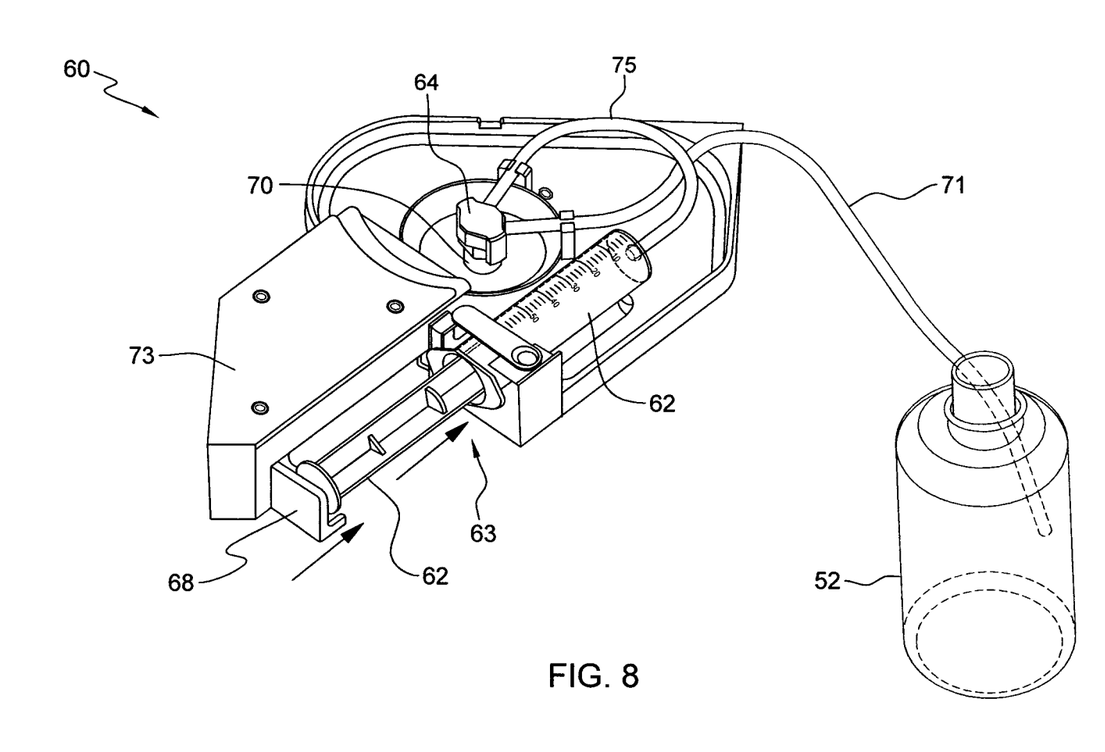
FIG. 8 is an expanded view of a sample handling apparatus, in accordance with one or more aspects of the present invention.
Figure 9A:
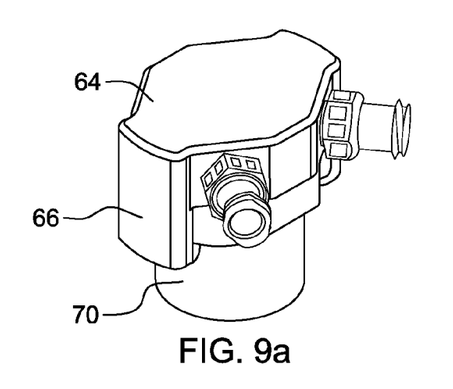
FIGS. 9a-d are various views of a sample cell insert mounted on sample cell in accordance with one or more aspects of the present invention.
Figure 9B:
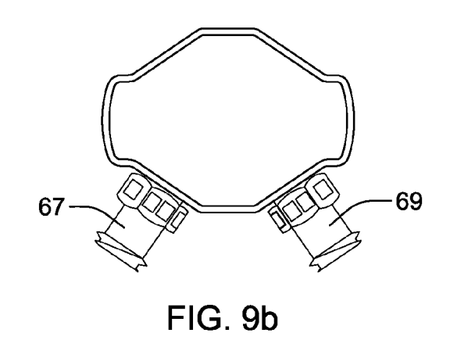
Figure 9C:
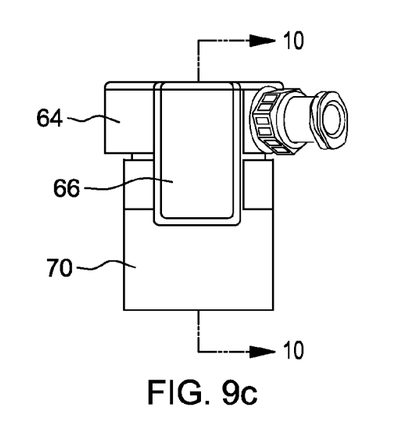
Figure 9D:
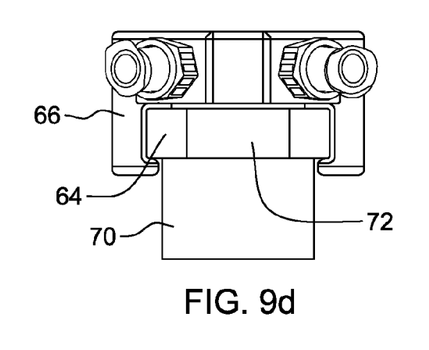

FIG. 8 is an expanded view of the sample handling apparatus of the accordance with one aspect of the present invention, including removable syringe 62 mounted therein using cradle/latch area 63. Motor 73 (detail not shown) is provided which drives an actuator 68 to activate the syringe plunger to expel sample (not shown for clarity). Motor 67 may programmably activate the actuator 68 to expel sample at a desired rate over a desired measurement time, depending on operator and/or pre-programmed preferences. This programming can be controlled together with, or separate from, other programming within analyzer 50. The syringe flows sample at the desired rate through tube 75, through flow cell insert 64, and then out tube 71 and into bottle 52.

FIGS. 9*a-d* are various views of the sample cell insert 64 mounted on a sample cell 70 in accordance with one aspect of the present invention. Sample cell insert "arms" 66 can be formed to affix to, e.g., grab, sample cell edges 74 upon a "quarter twist" of the insert after it is lower over cell faces 72. Sample cell insert/sample cell then form a combination, which can be gracefully placed into the analyzer 50. In this embodiment, the sample chamber of the analyzer need not be specially modified, i.e., the sample chamber still accepts a typical sample cell 70 form factor. Therefore, the analyzer 50 can be used for static non-flowing samples using plain sample cells, or in combination with the apparatus of the present invention for flowing sample.

Tube outlets 67 and 69 are also shown from which tubes are attachable and detachable. The present invention contemplates any of the subcomponents including insert 64, syringe 62 and tubes 75/71 to be either consumable (single use), semi-consumable (several uses) or fairly long-lasting (many uses). In an embodiment for crude oil measurement, the sample cell insert can be long lasting (e.g., cleanable stainless steel) with the syringes and tubes being consumable because they are more difficult to clean.

Figure 10:
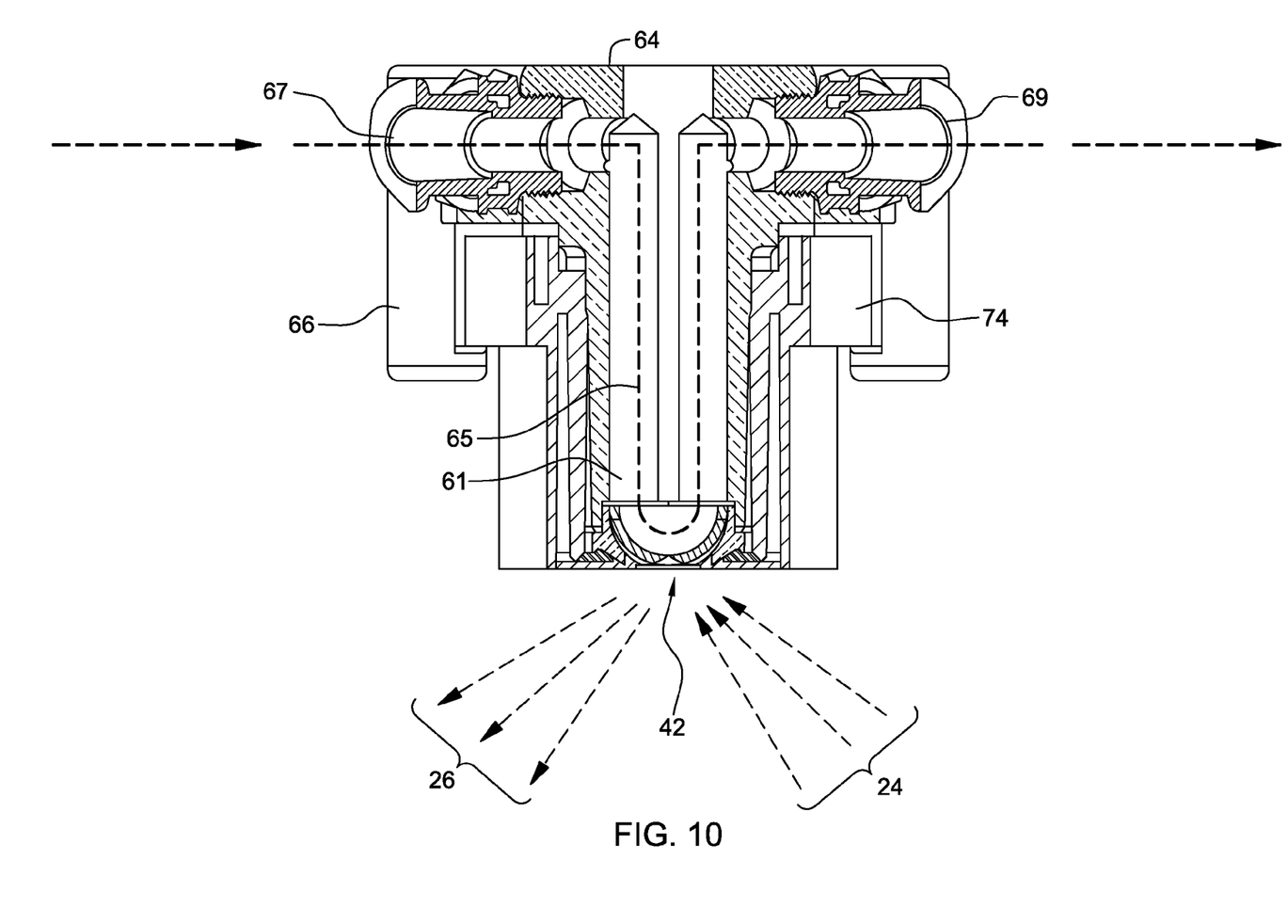
FIG. 10 is a detailed, cross-sectional view of the sample cell insert mounted on sample cell, in accordance with one or more aspects of the present invention.

FIG. 10 (where like elements are designated with like numerals from above) is a detailed, cross-sectional view of the sample cell insert 64 mounted on sample cell 70 in accordance with one aspect of the present invention. Shown here is additional internal detail of internal tube structures 61 of insert 64 which carry sample down into cell 70, toward the lower, filmed area thereof. The tube structures 61 open up through an aperture facing the sample cell film, so that the sample contacts the film of the sample cell, thereby presenting the flowing sample 65 through sample focal area or point 42 (formed by x-ray beams 24 and 26).

In an alternate embodiment, the sample cell insert itself can function as a sample cell of the analyzer, with its own film, omitting the need for attaching to a typical sample cell.

Figure 11A:
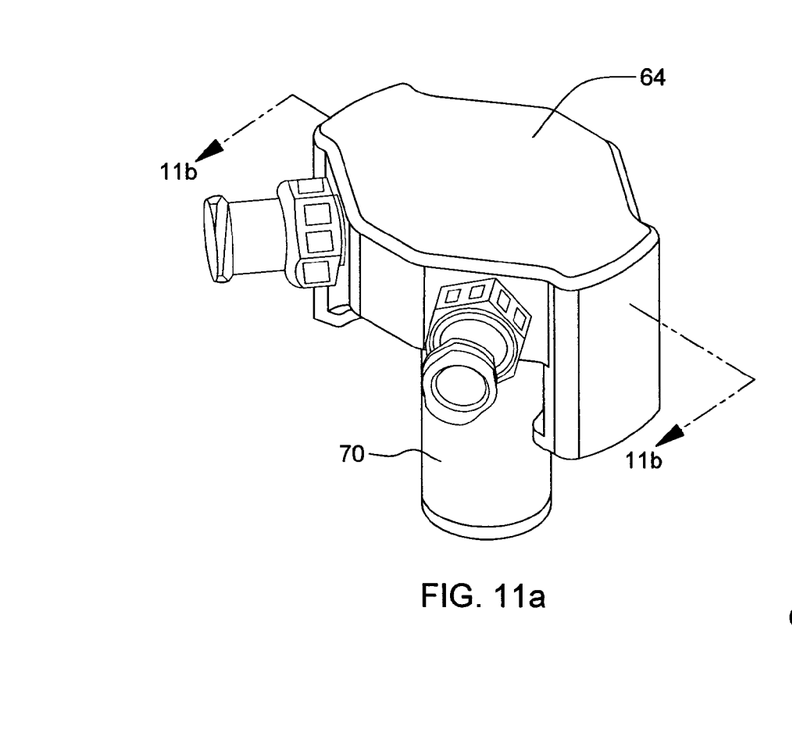
FIGS. 11a-b are perspective and sectional views, respectively, of a sample cell insert, in accordance with one or more aspects of the present invention.
Figure 11B:
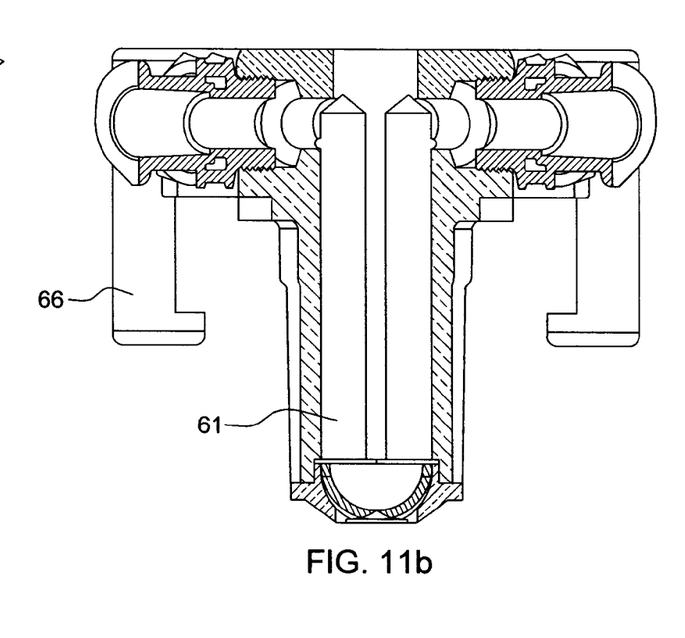

FIGS. 11*a*-*b* (where like elements are designated with like numerals from above) are perspective and sectional views of the sample cell insert in accordance with one aspect of the present invention, but shown without a sample cell.

Exemplary analytes measured in accordance with the present invention include: S, Cl, P, K, Ca, V, Mn, Fe, Co, Ni, Cu, Zn, Hg, As, Pb, and/or Se. These are analytes of particular interest for non-homogeneous crude oil.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A sample handling apparatus for a material analyzer, comprising:

a sample cell insert for carrying sample to and from a sample focal area of the analyzer;

a removable sample carrying device for providing sample to the sample cell insert; and a motorized actuator to flow sample from the carrying device to the sample cell insert through the sample focal area during the time period of measurement of the sample to thereby provide an average analyte concentration.

2. The sample handling apparatus of claim 1, wherein the removable sample carrying device is a syringe, and the actuator pushes a plunger of the syringe to expel the sample therefrom to the sample cell insert.

3. The sample handling apparatus of claim 1, wherein the sample cell insert is mounted onto a sample cell, the sample cell being insertable into the analyzer for sample analysis.

4. The sample handling apparatus of claim 1, in combination with an x-ray analyzer, the x-ray analyzer comprising an x-ray engine including:

an x-ray excitation path; and an x-ray detection path;

wherein the x-ray excitation and/or the x-ray detection path defines the sample focal area.

5. The combination of claim 4, wherein the focal area is a focal point.

6. The combination of claim 5, wherein the focal point is defined by focused x-rays to/from at least one focusing optic in the x-ray excitation path and/or the x-ray detection path.

7. The combination of claim 6, wherein the at least one focusing optic is at least one curved diffracting optic or polycapillary optic.

8. The combination of claim 6, wherein the at least one focusing optic is at least one focusing monochromatic optic.

9. The combination of claim 8, wherein the at least one focusing monochromatic optic is a curved crystal optic or curved multi-layer optic.

10. The combination of claim 5, wherein at least one focusing optic in the x-ray detection path is positioned such that an input focal point thereof is at the x-ray focal point, and corresponds to an output focal point of at least one focusing optic in the x-ray excitation path.

11. The combination of claim 4, wherein the x-ray analysis system comprises a monochromatic wavelength-enabled XRF analyzer.

12. The combination of claim 11, wherein the analyzer is an MWDXRF or ME-EDXRF analyzer.

13. The apparatus of any one of claims 1 through 12, wherein the sample comprises a petroleum-based product requiring the measurement of an analyte therein.

14. The apparatus of any one of claims 1 through 12, wherein an analyte measured is at least one element chosen from the following list: S, Cl, P, K, Ca, V, Mn, Fe, Co, Ni, Cu, Zn, Hg, As, Pb, and Se.

15. The apparatus of any one of claims 1 through 12 wherein the sample is crude oil, and an analyte measured is chlorine.

16. A sample handling method for a material analyzer, comprising:

using a sample cell insert for carrying sample to and from a sample focal area of the analyzer;

using a removable sample carrying device for providing sample to the sample cell insert; and activating a motorized actuator to flow sample from the carrying device to the sample cell insert through the sample focal area during the time period of measurement of the sample to thereby provide an average analyte concentration.

17. The sample handling method of claim 16, wherein the removable sample carrying device is a syringe, and the actuator pushes a plunger of the syringe to expel the sample therefrom to the sample cell insert.

18. The sample handling method of claim 17, further comprising:
    retrieving sample with the syringe; and
    inserting the syringe with sample into a sample handling apparatus including the sample cell insert and actuator.

19. The sample handling method of claim 16, wherein the sample cell insert is mounted onto a sample cell, the sample cell being insertable into the analyzer for sample analysis.

* * * * *